(12) United States Patent
Kokish et al.

(10) Patent No.: US 11,504,195 B2
(45) Date of Patent: *Nov. 22, 2022

(54) ACTIVE DRIVE MECHANISM FOR SIMULTANEOUS ROTATION AND TRANSLATION

(71) Applicant: Auris Health, Inc., Redwood City, CA (US)

(72) Inventors: Arkady Kokish, Los Gatos, CA (US); Francis Macnamara, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 506 days.

This patent is subject to a terminal disclaimer.

(21) Appl. No.: 16/669,268

(22) Filed: Oct. 30, 2019

(65) Prior Publication Data

US 2020/0129252 A1    Apr. 30, 2020

Related U.S. Application Data

(63) Continuation of application No. 15/359,886, filed on Nov. 23, 2016, now Pat. No. 10,524,867, which is a
(Continued)

(51) Int. Cl.
*A61B 34/30* (2016.01)
*A61B 90/00* (2016.01)
(Continued)

(52) U.S. Cl.
CPC ............. *A61B 34/30* (2016.02); *A61B 34/70* (2016.02); *A61B 34/35* (2016.02); *A61B 34/37* (2016.02);
(Continued)

(58) Field of Classification Search
CPC ......... A61B 34/30; A61B 34/70; A61B 34/37; A61B 2034/301; A61B 2017/22075; A61M 25/0113; A61M 25/09041
See application file for complete search history.

(56) References Cited

U.S. PATENT DOCUMENTS 2,556,601 A    6/1951   Schofield
2,566,183 A    8/1951   Forss
(Continued)

FOREIGN PATENT DOCUMENTS

CA    2285342    10/1998
CN    101161426    4/2008
(Continued)

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.
(Continued)

*Primary Examiner* — Katherine H Schwiker
(74) *Attorney, Agent, or Firm* — Frost Brown Todd LLC

(57) ABSTRACT

An exemplary drive apparatus may include a roller assembly and a roller support. The roller assembly may have a first continuous surface, a second continuous surface, an open configuration for receiving an elongate member, and a closed configuration for securing the elongate member in the roller assembly. The roller assembly imparts axial motion to the elongate member along the first continuous surface, which maintains contact with the elongate member during the axial motion. The roller support rotates the roller assembly about the second continuous surface, which maintains contact with the roller support during rotational motion. The
(Continued)

roller assembly and roller support to impart axial and rotational motion, respectively, independently of one another.

19 Claims, 8 Drawing Sheets

Related U.S. Application Data continuation of application No. 13/835,136, filed on Mar. 15, 2013, now abandoned.

(51) Int. Cl.
*A61B 34/00* (2016.01)
*A61B 34/35* (2016.01)
*A61B 34/37* (2016.01)

(52) U.S. Cl.
CPC ......... *A61B 90/37* (2016.02); *A61B 2034/301* (2016.02)

(56) References Cited

U.S. PATENT DOCUMENTS

| | | |
|---|---|---|
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,790,002 A | 2/1974 | Guilbaud et al. |
| 3,835,854 A | 9/1974 | Jewett |
| 3,921,536 A | 11/1975 | Savage |
| 3,926,386 A | 12/1975 | Stahmann |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,305 A | 7/1990 | Blood |
| 4,945,790 A | 8/1990 | Golden |
| 5,078,714 A | 1/1992 | Katims |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,339,799 A | 8/1994 | Kami et al. |
| 5,341,807 A | 8/1994 | Nardella |
| 5,350,101 A | 9/1994 | Godlewski |
| 5,368,015 A | 11/1994 | Wilk |
| 5,394,875 A | 3/1995 | Lewis et al. |
| 5,397,443 A | 3/1995 | Michaels |
| 5,398,691 A | 3/1995 | Martin et al. |
| 5,408,409 A | 4/1995 | Glassman et al. |
| 5,426,687 A | 6/1995 | Goodall et al. |
| 5,447,529 A | 9/1995 | Marchlinski et al. |
| 5,469,857 A | 11/1995 | Laurent et al. |
| 5,477,856 A | 12/1995 | Lundquist |
| 5,492,131 A | 2/1996 | Galel |
| 5,507,725 A | 4/1996 | Savage et al. |
| 5,524,180 A | 6/1996 | Wang et al. |
| 5,559,294 A | 9/1996 | Hoium et al. |
| 5,600,330 A | 2/1997 | Blood |
| 5,631,973 A | 5/1997 | Green |
| 5,662,108 A | 9/1997 | Budd et al. |
| 5,673,704 A | 10/1997 | Marchlinski et al. |
| 5,697,377 A | 12/1997 | Wittkampf |
| 5,709,661 A | 1/1998 | Van Egmond |
| 5,713,946 A | 2/1998 | Ben-Haim |
| 5,722,959 A | 3/1998 | Bierman |
| 5,738,096 A | 4/1998 | Ben-Haim |
| 5,749,362 A | 5/1998 | Funda et al. |
| 5,754,741 A | 5/1998 | Wang et al. |
| 5,762,458 A | 6/1998 | Wang et al. |
| 5,767,840 A | 6/1998 | Selker |
| 5,779,623 A | 7/1998 | Bonnell |
| 5,784,542 A | 7/1998 | Ohm et al. |
| 5,792,135 A | 8/1998 | Madhani et al. |
| 5,797,900 A | 8/1998 | Madhani |
| 5,799,055 A | 8/1998 | Peshkin et al. |
| 5,815,640 A | 9/1998 | Wang et al. |
| 5,825,982 A | 10/1998 | Wright et al. |
| 5,833,608 A | 11/1998 | Acker |
| 5,836,869 A | 11/1998 | Kudo et al. |
| 5,836,874 A | 11/1998 | Swanson et al. |
| 5,836,990 A | 11/1998 | Li |
| 5,842,390 A | 12/1998 | Bouligny |
| 5,843,076 A | 12/1998 | Webster, Jr. et al. |
| 5,845,646 A | 12/1998 | Lemelson |
| 5,855,583 A | 1/1999 | Wang et al. |
| 5,859,934 A | 1/1999 | Green |
| 5,876,325 A | 3/1999 | Mizuno et al. |
| 5,878,193 A | 3/1999 | Wang et al. |
| 5,891,095 A | 4/1999 | Eggers et al. |
| 5,921,968 A | 7/1999 | Lampropoulos et al. |
| 5,925,078 A | 7/1999 | Anderson |
| 5,935,079 A | 8/1999 | Swanson et al. |
| 5,950,629 A | 9/1999 | Taylor et al. |
| 5,951,475 A | 9/1999 | Gueziec et al. |
| 5,953,683 A | 9/1999 | Hansen et al. |
| 5,967,934 A | 10/1999 | Ishida et al. |
| 5,983,126 A | 11/1999 | Wittkampf |
| 6,004,271 A | 12/1999 | Moore |
| 6,061,587 A | 5/2000 | Kucharczyk et al. |
| 6,063,022 A | 5/2000 | Ben-Haim |
| 6,063,095 A | 5/2000 | Wang et al. |
| 6,077,219 A | 6/2000 | Viebach |
| 6,080,181 A | 6/2000 | Jensen et al. |
| 6,083,170 A | 7/2000 | Ben-Haim |
| 6,084,371 A | 7/2000 | Kress et al. |
| 6,096,004 A | 8/2000 | Meglan et al. |
| 6,106,511 A | 8/2000 | Jensen |
| 6,129,668 A | 10/2000 | Haynor et al. |
| 6,132,368 A | 10/2000 | Cooper |
| 6,154,000 A | 11/2000 | Rastegar et al. |
| 6,161,032 A | 12/2000 | Acker |
| 6,171,234 B1 | 1/2001 | White et al. |
| 6,172,499 B1 | 1/2001 | Ashe |
| 6,185,478 B1 | 2/2001 | Koakutsu et al. |
| 6,203,493 B1 | 3/2001 | Ben-Haim |
| 6,226,543 B1 | 5/2001 | Gilboa et al. |
| 6,228,028 B1 | 5/2001 | Klein et al. |
| 6,233,476 B1 | 5/2001 | Strommer et al. |
| 6,233,504 B1 | 5/2001 | Das et al. |
| 6,246,200 B1 | 6/2001 | Blumenkranz et al. |
| 6,259,806 B1 | 7/2001 | Green |
| 6,266,551 B1 | 7/2001 | Osadchy et al. |
| 6,272,371 B1 | 8/2001 | Shlomo |
| 6,289,579 B1 | 9/2001 | Viza et al. |
| 6,301,496 B1 | 10/2001 | Reisfeld |
| 6,309,397 B1 | 10/2001 | Julian et al. |
| 6,310,828 B1 | 10/2001 | Mumm et al. |
| 6,312,435 B1 | 11/2001 | Wallace et al. |
| 6,331,181 B1 | 12/2001 | Tierney et al. |
| 6,363,279 B1 | 3/2002 | Ben-Haim et al. |
| 6,370,411 B1 | 4/2002 | Osadchy et al. |
| 6,371,952 B1 | 4/2002 | Madhani et al. |
| 6,375,471 B1 | 4/2002 | Wendlandt et al. |
| 6,380,732 B1 | 4/2002 | Gilboa |
| 6,381,483 B1 | 4/2002 | Hareyama et al. |

(56) References Cited

U.S. PATENT DOCUMENTS

| | | |
|---|---|---|
| 6,384,483 B1 | 5/2002 | Igarashi et al. |
| 6,393,340 B2 | 5/2002 | Funda et al. |
| 6,394,998 B1 | 5/2002 | Wallace et al. |
| 6,398,731 B1 | 6/2002 | Mumm et al. |
| 6,400,979 B1 | 6/2002 | Stoianovici et al. |
| 6,401,572 B1 | 6/2002 | Provost |
| 6,415,171 B1 | 7/2002 | Gueziec et al. |
| 6,424,885 B1 | 7/2002 | Niemeyer et al. |
| 6,436,107 B1 | 8/2002 | Wang et al. |
| 6,487,940 B2 | 12/2002 | Hart et al. |
| 6,491,701 B2 | 12/2002 | Tierney et al. |
| 6,493,573 B1 | 12/2002 | Martinelli et al. |
| 6,493,608 B1 | 12/2002 | Niemeyer |
| 6,530,913 B1 | 3/2003 | Giba et al. |
| 6,544,230 B1 | 4/2003 | Flaherty |
| 6,550,128 B1 | 4/2003 | Lorenz |
| 6,551,273 B1 | 4/2003 | Olson et al. |
| 6,565,554 B1 | 5/2003 | Niemeyer |
| 6,574,355 B2 | 6/2003 | Green |
| 6,580,938 B1 | 6/2003 | Acker |
| 6,587,750 B2 | 7/2003 | Gerbi et al. |
| 6,594,552 B1 | 7/2003 | Nowlin |
| 6,610,007 B2 | 8/2003 | Belson et al. |
| 6,615,155 B2 | 9/2003 | Gilboa |
| 6,618,612 B1 | 9/2003 | Acker et al. |
| 6,620,173 B2 | 9/2003 | Gerbi et al. |
| 6,626,899 B2 | 9/2003 | Houser et al. |
| 6,629,534 B1 | 10/2003 | St. Goar et al. |
| 6,659,939 B2 | 12/2003 | Moll et al. |
| 6,669,709 B1 | 12/2003 | Cohn |
| 6,685,698 B2 | 2/2004 | Morley et al. |
| 6,695,818 B2 | 2/2004 | Wollschlager |
| 6,699,235 B2 | 3/2004 | Wallace et al. |
| 6,716,166 B2 | 4/2004 | Govari |
| 6,726,675 B1 | 4/2004 | Beyar |
| 6,741,883 B2 | 5/2004 | Gildenberg |
| 6,774,624 B2 | 8/2004 | Anderson et al. |
| 6,783,524 B2 | 8/2004 | Anderson et al. |
| 6,786,896 B1 | 9/2004 | Madhani et al. |
| 6,799,065 B1 | 9/2004 | Niemeyer |
| 6,817,973 B2 | 11/2004 | Merril et al. |
| 6,817,974 B2 | 11/2004 | Cooper et al. |
| 6,827,712 B2 | 12/2004 | Tovey et al. |
| 6,852,107 B2 | 2/2005 | Wang et al. |
| 6,858,003 B2 | 2/2005 | Evans et al. |
| 6,905,460 B2 | 6/2005 | Wang et al. |
| 6,963,792 B1 | 11/2005 | Green |
| 7,021,173 B2 | 4/2006 | Stoianovici et al. |
| 7,044,936 B2 | 5/2006 | Harding |
| 7,074,179 B2 | 7/2006 | Wang et al. |
| 7,087,049 B2 | 8/2006 | Nowlin et al. |
| 7,155,315 B2 | 12/2006 | Niemeyer et al. |
| 7,169,141 B2 | 1/2007 | Brock et al. |
| 7,172,580 B2 | 2/2007 | Hruska et al. |
| 7,225,012 B1 | 5/2007 | Susil et al. |
| 7,276,044 B2 | 10/2007 | Ferry et al. |
| 7,280,863 B2 | 10/2007 | Shachar |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock |
| 7,404,824 B1 | 7/2008 | Webler et al. |
| 7,494,494 B2 | 2/2009 | Stoianovici et al. |
| 7,540,866 B2 | 6/2009 | Viswanathan et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,850,642 B2 | 12/2010 | Moll et al. |
| 7,938,809 B2 | 5/2011 | Lampropoulos et al. |
| 7,963,288 B2 | 6/2011 | Rosenberg et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,092,397 B2 | 1/2012 | Wallace et al. |
| 8,126,534 B2 | 2/2012 | Maschke |
| 8,157,308 B2 | 4/2012 | Pedersen |
| 8,182,415 B2 | 5/2012 | Larkin et al. |
| 8,190,238 B2 | 5/2012 | Moll et al. |
| 8,202,244 B2 | 6/2012 | Cohen et al. |
| 8,219,178 B2 | 7/2012 | Smith et al. |
| 8,235,942 B2 | 8/2012 | Frassica et al. |
| 8,244,327 B2 | 8/2012 | Fichtinger et al. |
| 8,277,417 B2 | 10/2012 | Fedinec et al. |
| 8,291,791 B2 | 10/2012 | Light et al. |
| 8,343,040 B2 | 1/2013 | Frassica et al. |
| 8,414,505 B1 | 4/2013 | Weitzner |
| 8,425,465 B2 | 4/2013 | Nagano |
| 8,498,691 B2 | 7/2013 | Moll et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,827,948 B2 | 9/2014 | Romo et al. |
| 8,870,815 B2 | 10/2014 | Bhat et al. |
| 8,894,610 B2 | 11/2014 | MacNamara et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,023,068 B2 | 5/2015 | Viola |
| 9,138,166 B2 | 9/2015 | Wong et al. |
| 9,173,713 B2 | 11/2015 | Hart et al. |
| 9,204,933 B2 | 12/2015 | Reis et al. |
| 9,254,123 B2 | 2/2016 | Alvarez et al. |
| 9,259,281 B2 | 2/2016 | Griffiths et al. |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,258,285 B2 | 4/2019 | Hauck |
| 10,285,574 B2 | 5/2019 | Landey et al. |
| 10,299,870 B2 | 5/2019 | Connolly et al. |

(56) References Cited

U.S. PATENT DOCUMENTS

| | | |
|---|---|---|
| 10,314,463 B2 | 6/2019 | Agrawal et al. |
| 10,363,103 B2 | 7/2019 | Alvarez et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,463,439 B2 | 11/2019 | Joseph et al. |
| 10,464,209 B2 | 11/2019 | Ho et al. |
| 10,470,830 B2 | 11/2019 | Hill |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,524,867 B2 | 1/2020 | Kokish et al. |
| 10,539,478 B2 | 1/2020 | Lin |
| 10,543,048 B2 | 1/2020 | Noonan et al. |
| 10,555,778 B2 | 2/2020 | Ummalaneni et al. |
| 10,556,092 B2 | 2/2020 | Yu et al. |
| 10,569,052 B2 | 2/2020 | Kokish et al. |
| 10,639,114 B2 | 5/2020 | Schuh |
| 10,765,487 B2 | 9/2020 | Ho |
| 2001/0009976 A1 | 7/2001 | Panescu et al. |
| 2001/0029366 A1 | 10/2001 | Swanson et al. |
| 2001/0042643 A1 | 11/2001 | Krueger et al. |
| 2002/0045905 A1 | 4/2002 | Gerbi et al. |
| 2002/0087169 A1 | 7/2002 | Brock et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0138009 A1 | 9/2002 | Brockway et al. |
| 2002/0156369 A1 | 10/2002 | Chakeres |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0050649 A1 | 3/2003 | Brock et al. |
| 2003/0056561 A1 | 3/2003 | Butscher et al. |
| 2003/0073908 A1 | 4/2003 | Desai |
| 2003/0074011 A1 | 4/2003 | Gilboa et al. |
| 2003/0109780 A1 | 6/2003 | Coste-Maniere et al. |
| 2003/0135204 A1 | 7/2003 | Lee et al. |
| 2003/0167623 A1 | 9/2003 | Lorenz |
| 2003/0212308 A1 | 11/2003 | Bendall |
| 2004/0015053 A1 | 1/2004 | Bieger |
| 2004/0034282 A1 | 2/2004 | Quaid, III |
| 2004/0034365 A1 | 2/2004 | Lentz et al. |
| 2004/0152972 A1 | 8/2004 | Hunter |
| 2004/0171929 A1 | 9/2004 | Leitner et al. |
| 2004/0176751 A1 | 9/2004 | Weitzner et al. |
| 2004/0220588 A1 | 11/2004 | Kermode et al. |
| 2004/0243147 A1 | 12/2004 | Lipow |
| 2004/0254566 A1 | 12/2004 | Plicchi |
| 2005/0004579 A1 | 1/2005 | Schneider et al. |
| 2005/0027397 A1 | 2/2005 | Niemeyer |
| 2005/0059960 A1 | 3/2005 | Simaan et al. |
| 2005/0131460 A1 | 6/2005 | Gifford, III et al. |
| 2005/0159789 A1 | 7/2005 | Brockway et al. |
| 2005/0165276 A1 | 7/2005 | Belson et al. |
| 2005/0177026 A1 | 8/2005 | Hoeg et al. |
| 2005/0182295 A1 | 8/2005 | Soper et al. |
| 2005/0182330 A1 | 8/2005 | Brockway et al. |
| 2005/0183532 A1 | 8/2005 | Najaf et al. |
| 2005/0200324 A1 | 9/2005 | Guthart et al. |
| 2005/0203382 A1 | 9/2005 | Govari et al. |
| 2005/0222554 A1 | 10/2005 | Wallace et al. |
| 2006/0013523 A1 | 1/2006 | Childers et al. |
| 2006/0025676 A1 | 2/2006 | Viswanathan et al. |
| 2006/0041245 A1 | 2/2006 | Ferry |
| 2006/0058647 A1 | 3/2006 | Strommer et al. |
| 2006/0111692 A1 | 5/2006 | Hlavka et al. |
| 2006/0146010 A1 | 7/2006 | Schneider |
| 2006/0178556 A1 | 8/2006 | Hasser et al. |
| 2006/0200049 A1 | 9/2006 | Leo et al. |
| 2006/0201688 A1 | 9/2006 | Jenner et al. |
| 2006/0229587 A1 | 10/2006 | Beyar et al. |
| 2006/0229641 A1 | 10/2006 | Gupta et al. |
| 2006/0237205 A1 | 10/2006 | Sia et al. |
| 2006/0271036 A1 | 11/2006 | Garabedian et al. |
| 2007/0000498 A1 | 1/2007 | Glynn et al. |
| 2007/0013336 A1 | 1/2007 | Nowlin et al. |
| 2007/0038181 A1 | 2/2007 | Melamud et al. |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0100201 A1 | 5/2007 | Komiya et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0123851 A1 | 5/2007 | Alejandro et al. |
| 2007/0149946 A1 | 6/2007 | Viswanathan |
| 2007/0185485 A1 | 8/2007 | Hauck et al. |
| 2007/0185486 A1 | 8/2007 | Hauck et al. |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0249901 A1 | 10/2007 | Ohline et al. |
| 2007/0287999 A1 | 12/2007 | Malecki et al. |
| 2007/0293724 A1 | 12/2007 | Saadat et al. |
| 2007/0299427 A1 | 12/2007 | Yeung et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0039255 A1 | 2/2008 | Jinno et al. |
| 2008/0046122 A1 | 2/2008 | Manzo et al. |
| 2008/0064920 A1 | 3/2008 | Bakos et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0183071 A1 | 7/2008 | Strommer et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0300592 A1 | 12/2008 | Weitzner et al. |
| 2008/0302200 A1 | 12/2008 | Tobey |
| 2008/0319311 A1 | 12/2008 | Hamadeh |
| 2009/0005768 A1 | 1/2009 | Sharareh |
| 2009/0054884 A1 | 2/2009 | Farley et al. |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0131872 A1 | 5/2009 | Popov |
| 2009/0163948 A1 | 6/2009 | Sunaoshi |
| 2009/0171371 A1 | 7/2009 | Nixon |
| 2009/0221908 A1 | 9/2009 | Glossop |
| 2009/0247944 A1 | 10/2009 | Kirschenman et al. |
| 2009/0248039 A1 | 10/2009 | Cooper et al. |
| 2009/0318797 A1 | 12/2009 | Hadani |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081920 A1 | 4/2010 | Whitmore, III et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0187740 A1 | 7/2010 | Orgeron |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0249506 A1 | 9/2010 | Prisco et al. |
| 2010/0274078 A1 | 10/2010 | Kim et al. |
| 2010/0280320 A1 | 11/2010 | Alvarez et al. |
| 2010/0280525 A1 | 11/2010 | Alvarez et al. |
| 2010/0332033 A1 | 12/2010 | Diolaiti |
| 2011/0015484 A1 | 1/2011 | Alvarez et al. |

(56) References Cited

U.S. PATENT DOCUMENTS

| | | |
|---|---|---|
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0016346 A1 | 1/2012 | Steinmetz et al. |
| 2012/0046652 A1 | 2/2012 | Sokel |
| 2012/0316393 A1 | 2/2012 | Frassica et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0132018 A1 | 5/2012 | Tang |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0245595 A1 | 9/2012 | Kesavadas et al. |
| 2012/0277730 A1 | 11/2012 | Salahieh |
| 2012/0283747 A1 | 11/2012 | Popovic |
| 2012/0310112 A1 | 12/2012 | Fichtinger et al. |
| 2013/0012779 A1 | 1/2013 | Frassica et al. |
| 2013/0018400 A1 | 1/2013 | Milton et al. |
| 2013/0030363 A1 | 1/2013 | Wong et al. |
| 2013/0066335 A1 | 3/2013 | Barwinkel |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0180063 A1 | 6/2014 | Zhao |
| 2014/0222019 A1 | 8/2014 | Brudnick |
| 2014/0243849 A1 | 8/2014 | Saglam et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277333 A1 | 9/2014 | Lewis et al. |
| 2014/0277334 A1 | 9/2014 | Yu et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2015/0012134 A1 | 1/2015 | Robinson |
| 2015/0090063 A1 | 4/2015 | Lantermann et al. |
| 2015/0133858 A1 | 5/2015 | Julian et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0182250 A1 | 7/2015 | Conlon et al. |
| 2015/0231364 A1 | 8/2015 | Blanchard |
| 2015/0327939 A1 | 11/2015 | Kokish et al. |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0007881 A1 | 1/2016 | Wong et al. |
| 2016/0157945 A1 | 6/2016 | Madhani |
| 2016/0166234 A1 | 6/2016 | Zhang |
| 2016/0192860 A1 | 7/2016 | Allenby |
| 2016/0206389 A1 | 7/2016 | Miller |
| 2016/0213435 A1 | 7/2016 | Hourtash |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374590 A1 | 12/2016 | Wong et al. |
| 2017/0007337 A1 | 1/2017 | Dan |
| 2017/0007343 A1 | 1/2017 | Yu |
| 2017/0119481 A1 | 5/2017 | Romo et al. |
| 2017/0151028 A1 | 6/2017 | Ogawa et al. |
| 2017/0165011 A1 | 6/2017 | Bovay et al. |
| 2017/0202627 A1 | 7/2017 | Sramek et al. |
| 2017/0209073 A1 | 7/2017 | Sramek et al. |
| 2017/0252540 A1 | 9/2017 | Weitzner et al. |
| 2017/0258534 A1 | 9/2017 | Hourtash |
| 2017/0281049 A1 | 10/2017 | Yamamoto |
| 2017/0290631 A1 | 10/2017 | Lee et al. |
| 2017/0325932 A1 | 11/2017 | Hoelzle |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0056044 A1 | 3/2018 | Choi et al. |
| 2018/0104820 A1 | 4/2018 | Troy et al. |
| 2018/0116735 A1 | 5/2018 | Tierney et al. |
| 2018/0206927 A1 | 7/2018 | Prisco et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223967 A1 | 7/2019 | Abbott |
| 2019/0223974 A1 | 7/2019 | Romo |
| 2019/0228525 A1 | 7/2019 | Mintz et al. |
| 2019/0231458 A1 | 8/2019 | DiMaio |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |

(56) References Cited

U.S. PATENT DOCUMENTS

| | | | |
|---|---|---|---|
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0008874 A1 | 1/2020 | Barbagli et al. |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155245 A1 | 5/2020 | Yu |
| 2020/0155801 A1 | 5/2020 | Kokish |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 103037799 | 4/2011 |
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102834043 | 12/2012 |
| CN | 102973317 | 3/2013 |
| CN | 102015759 | 4/2013 |
| CN | 103735313 | 4/2014 |
| CN | 105147393 | 12/2015 |
| CN | 105559850 | 5/2016 |
| CN | 105559886 | 5/2016 |
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| JP | 07-136173 | 5/1995 |
| JP | 2009-139187 | 6/2009 |
| JP | 2010-046384 | 3/2010 |
| WO | WO 97/44089 | 11/1997 |
| WO | WO 00/11495 | 3/2000 |
| WO | WO 00/45193 | 8/2000 |
| WO | WO 02/74178 | 9/2002 |
| WO | WO 03/077769 | 9/2003 |
| WO | WO 03/086190 | 10/2003 |
| WO | WO 03/091839 | 11/2003 |
| WO | WO 05/087128 | 9/2005 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO 14/028699 | 2/2014 |
| WO | WO 14/028702 | 2/2014 |
| WO | WO 15/127231 | 8/2015 |
| WO | WO 17/151993 | 9/2017 |

OTHER PUBLICATIONS

Extended European Search Report dated Feb. 6, 2015 in patent application No. 14160068.4, 6 pp.
European Search Report for European Patent Application No. 14160078.3 dated Feb. 11, 2015. (6 pages).
International Search Report for International Patent Application No. PCT/US2005/007108, dated Jun. 27, 2005 (4 pages).
Written Opinion of the International Searching Authority for International Patent Application No. PCT/US2005/007108, dated Jun. 27, 2005 (6 pages).
International Search Report for International Patent Application No. PCT/US2006/026218, dated Dec. 12, 2006 (4 pages).
Written Opinion of the International Searching Authority for International Patent Application No. PCT/US2006/026218, dated Dec. 12, 2006 (7 pages).
International Preliminary Report on Patentability for International Patent Application No. PCT/US2007/062617, dated Aug. 26, 2008 (7 pages).
European Examination Report dated Mar. 13, 2019 for Application No. EP 14160068.4, 4 pgs.
European Examination Report, Result of Consultation, dated May 28, 2021 for Application No. EP 14160068.4, 4 pgs.

ACTIVE DRIVE MECHANISM FOR SIMULTANEOUS ROTATION AND TRANSLATION

CROSS-REFERENCE TO RELATED APPLICATION

This application is a continuation of U.S. patent application Ser. No. 15/359,886, filed Nov. 23, 2016, entitled "ACTIVE DRIVE MECHANISM FOR SIMULTANEOUS ROTATION AND TRANSLATION," which is a continuation of U.S. patent application Ser. No. 13/835,136, filed Mar. 15, 2013 entitled "ACTIVE DRIVE MECHANISM FOR SIMULTANEOUS ROTATION AND TRANSLATION". The disclosure of each of the above is incorporated herein by reference in its entirety.

BACKGROUND

Robotic interventional systems and devices are well suited for performing minimally invasive medical procedures as opposed to conventional techniques wherein the patient's body cavity is open to permit the surgeon's hands access to internal organs. However, advances in technology have led to significant changes in the field of medical surgery such that less invasive surgical procedures, in particular, minimally invasive surgery (MIS), are increasingly popular.

MIS is generally defined as surgery that is performed by entering the body through the skin, a body cavity, or an anatomical opening utilizing small incisions rather than large, open incisions in the body. With MIS, it is possible to achieve less operative trauma for the patient, reduced hospitalization time, less pain and scarring, reduced incidence of complications related to surgical trauma, lower costs, and a speedier recovery.

Special medical equipment may be used to perform MIS procedures. Typically, a surgeon inserts small tubes or ports into a patient and uses endoscopes or laparoscopes having a fiber optic camera, light source, or miniaturized surgical instruments. Without a traditional large and invasive incision, the surgeon is not able to see directly into the patient. Thus, the video camera serves as the surgeon's eyes. The images of the interior of the body are transmitted to an external video monitor to allow a surgeon to analyze the images, make a diagnosis, visually identify internal features, and perform surgical procedures based on the images presented on the monitor.

MIS devices and techniques have advanced to the point where an insertion and rolling motion of components of an elongated component such as a catheter instrument, e.g., a catheter sheath and associated guidewire, are generally controllable by selectively operating rollers or other mechanisms for generally gripping the component. Some known mechanisms use gripping devices capable of infinite motion for translation, e.g., a roller, may require complex catheter component loading procedures, or may not be compatible with replaceable components adapted for a sterile operating environment.

Accordingly, there is a need in the art for systems and methods for inserting and rolling catheter components that address or solve the above problems.

SUMMARY

An exemplary drive apparatus is disclosed having a roller assembly configured to impart axial motion to the elongate member along a first continuous surface configured to maintain contact with the elongate member during axial motion. The drive apparatus may further include a roller support configured to rotate the roller assembly, thereby imparting rotational motion to the elongate member. The roller support may be configured to rotate the roller assembly about a second continuous surface configured to maintain contact with the roller support during rotational motion. Moreover, the roller assembly and roller support may be configured to impart axial and rotational motion independently of one another, such that a first one of the roller assembly and the roller support imparts their associated motion regardless of a presence or absence of motion by the other of the roller assembly and the roller support.

BRIEF DESCRIPTION OF THE DRAWINGS

While the claims are not limited to the illustrated embodiments, an appreciation of various aspects is best gained through a discussion of various examples thereof. Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limiting or restricting to the precise form and configuration shown in the drawings and disclosed in the following detailed description. Exemplary embodiments of the present invention are described in detail by referring to the drawings as follows.

DETAILED DESCRIPTION

Figure 1:
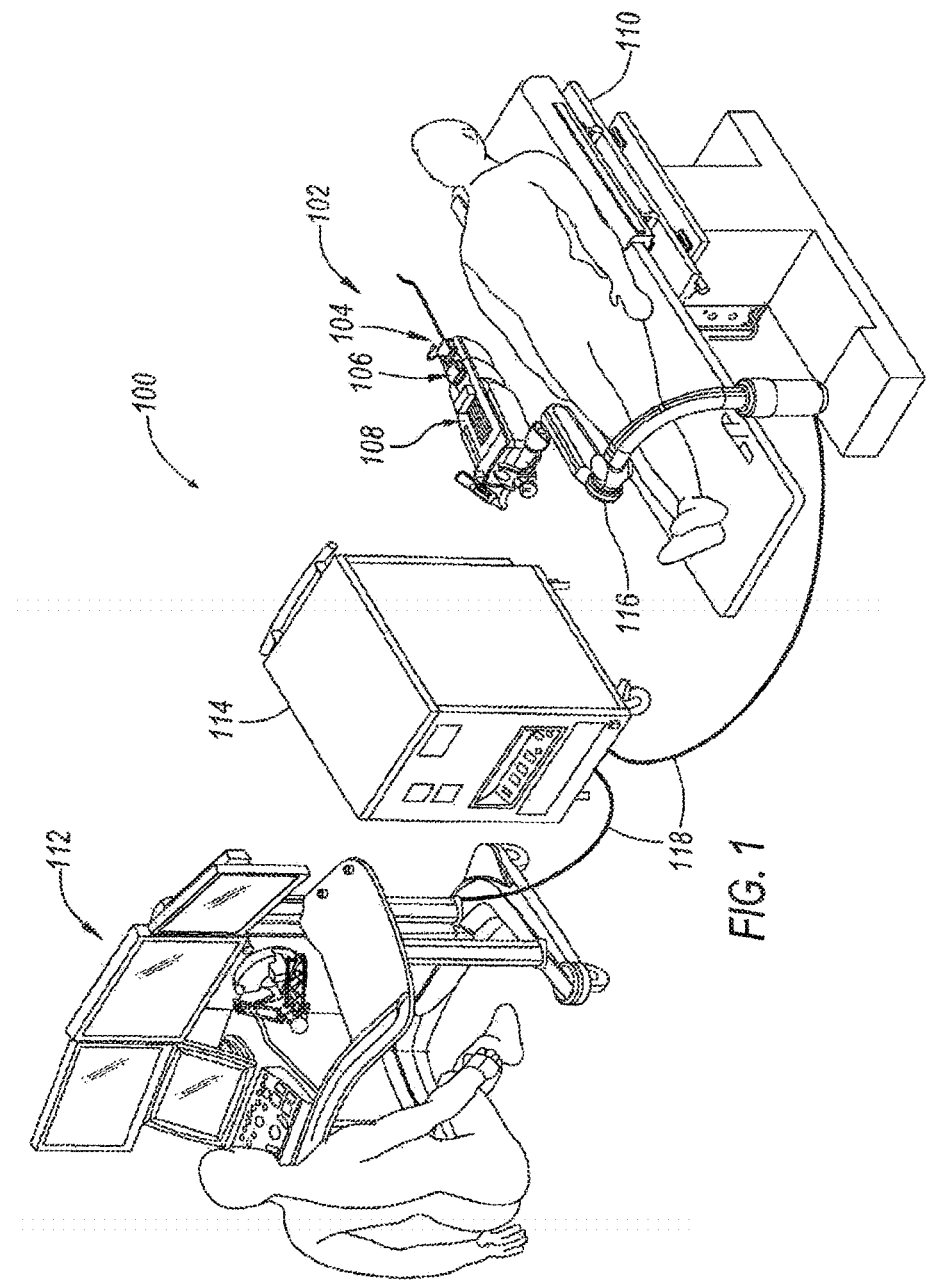
FIG. 1 is an illustration of a robotically controlled surgical system, according to one exemplary illustration.

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

Referring to FIG. 1, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter" or "catheter instrument"). Catheter assembly 102 is controllable using a robotic instrument driver 108 (generally referred to as "instrument driver"). During use, a patient is positioned on an operating table or surgical bed 110 (generally referred to as "operating table") to which robotic instrument driver 108 may be coupled or mounted. In the illustrated example, system 100 includes an operator workstation 112, an electronics rack 114 and associated bedside electronics box (not shown), a setup joint mounting brace 116, and instrument driver 108. A surgeon is seated at operator workstation 112 and can monitor the surgical procedure, patient vitals, and control one or more catheter devices. Operator workstation 112 may include a computer monitor to display a three dimensional object, such as a catheter instrument or component thereof, e.g., a guidewire, catheter sheath. Moreover, catheter instrument 502 may be displayed within or relative to a three dimensional space, such as a body cavity or organ, e.g., a chamber of a patient's heart. In one example, an operator uses a computer mouse to move a control point around the display to control the position of catheter instrument.

System components may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

Figure 2:
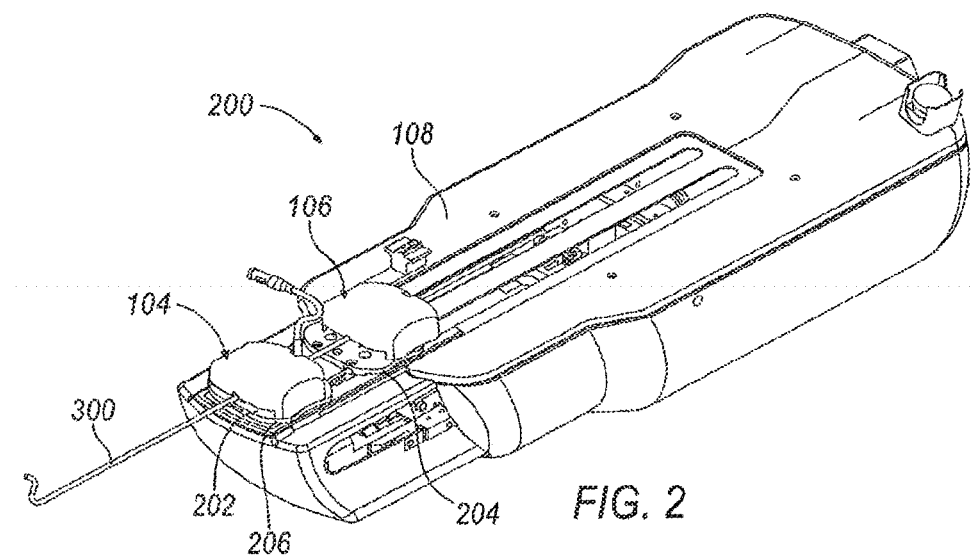
FIG. 2 is an illustration of an exemplary catheter assembly of the surgical system of FIG. 1.

Referring now to FIG. 2, an exemplary instrument assembly 200 is shown, including sheath instrument 104 and the associated guide or catheter instrument 106 mounted to mounting plates 202, 204 on a top portion of instrument driver 108. During use, catheter instrument 106 is inserted within a central lumen of sheath instrument 104 such that instruments 104, 106 are arranged in a coaxial manner. Although instruments 104, 106 are arranged coaxially, movement of each instrument 104, 106 can be controlled and manipulated independently. For this purpose, motors within instrument driver 108 are controlled such that carriages coupled to each of the instruments 104, 160 may allow the instruments 104, 106 to be driven forwards and backwards along the driver 108, e.g., with mounting plates securing the instruments to the driver 108 on bearings. As a result, a catheter 300 coupled to guide catheter instrument 106 and sheath instrument 104 can be controllably manipulated while inserted into the patient, as will be further illustrated. Additional instrument driver 108 motors (not shown in FIG. 2) may be activated to control bending of the catheter as well as the orientation of the distal tips thereof, including tools mounted at the distal tip. Sheath catheter instrument 106 is configured to move forward and backward for effecting an axial motion of the catheter, e.g., to insert and withdraw the catheter from a patient, respectively.

Figure 3:
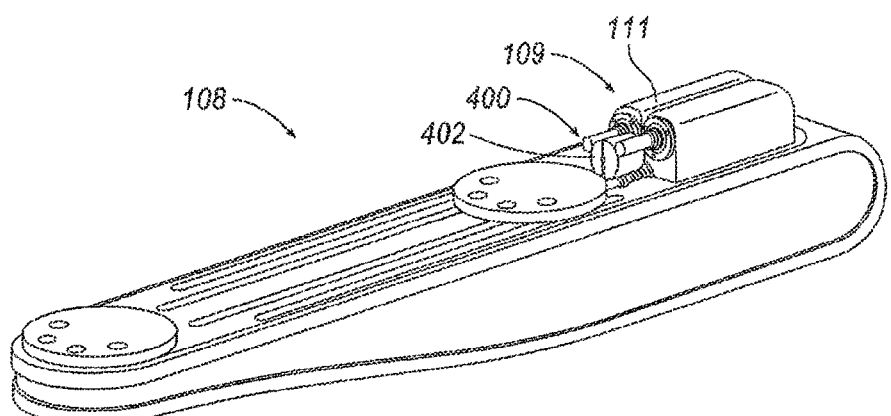
FIG. 3 is another exemplary illustration of an exemplary catheter assembly of the surgical system of FIG. 1.

Referring now to FIG. 3, another exemplary instrument 109 is illustrated mounted on the exemplary instrument driver 108. The instrument 109 includes a cover 111 and a drive apparatus 400 partially extending out of the cover, as will be described further in regard to FIGS. 4-11. More specifically, as will be described further, the drive apparatus 400 may include a disposable portion 402 which extends out of the housing 111, while an associated drive mechanism (not seen in FIG. 3) remains within the housing 111. Accordingly, the drive mechanism (not shown in FIG. 3) may generally be reused for surgical procedures, while the disposable portion 402 may part of a sterile environment associated with a surgical procedure and may be disposed of afterwards. Moreover, as will be described further below the disposable portion 402 may be formed of relatively cost-effective materials and may be of a generally small relative size, minimizing a length of the elongate member that must be allowed for the drive mechanism 400 to properly "grip" the elongate member, and increasing cost-effectiveness of the system 100 overall.

During use the instrument 109 may be used to manipulate an elongate member included in the catheter assembly 102, e.g., a catheter guidewire (not shown in FIG. 3). Alternatively, the instrument 109 may be employed to manipulate a catheter sheath (not shown in FIG. 3). Although a single instrument 109 is illustrated in FIG. 3, in another exemplary illustration two instruments 109 may be employed in which a first instrument 109 is used to insert and roll a guidewire, which guidewire is inserted within a central lumen of a second instrument 109 (not shown in FIG. 3) such that the two instruments 109 are arranged in a coaxial manner, substantially as described above regarding the instruments 104, 106. Additionally, the instruments 109 may generally insert and rotate the associated elongate member, i.e., the guidewire and catheter sheath, independently, as described above regarding the instruments 104, 106. Accordingly, while the exemplary illustrations herein may generally focus on the insertion and rotation of a guidewire for a catheter, the instrument 109 may be used for insertion and rotation of any elongate member that is convenient.

Figure 4:
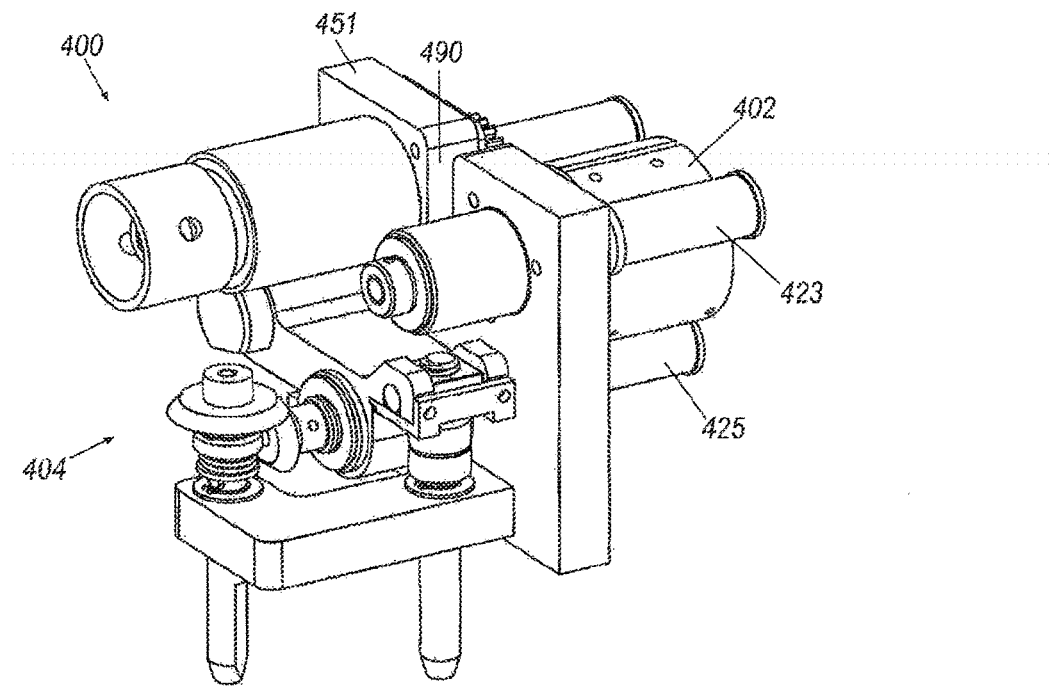
FIG. 4 is a rear perspective view of an exemplary drive apparatus for an elongated member, e.g., a guidewire for a catheter.
Figure 5:
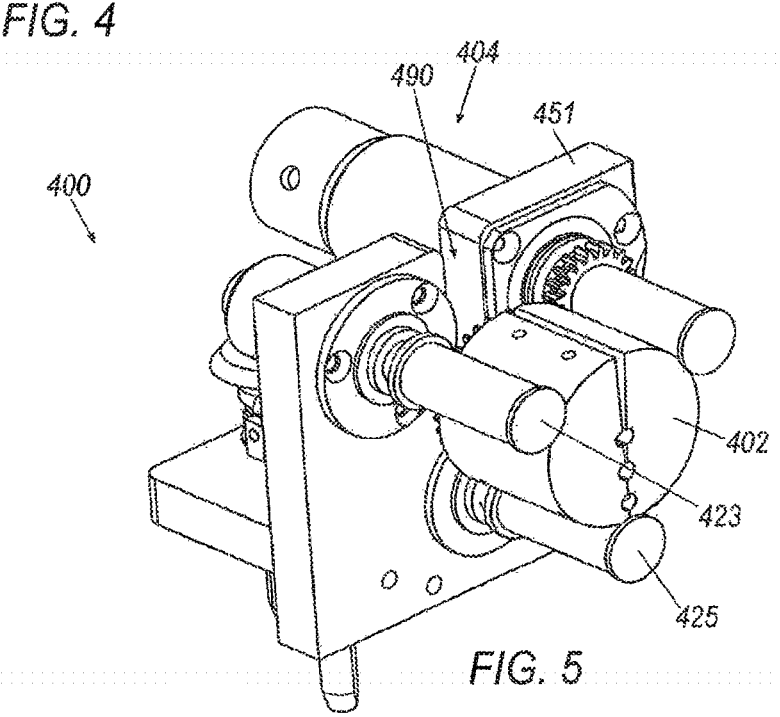
FIG. 5 is a front perspective view of the exemplary drive apparatus of FIG. 4.
Figure 6:
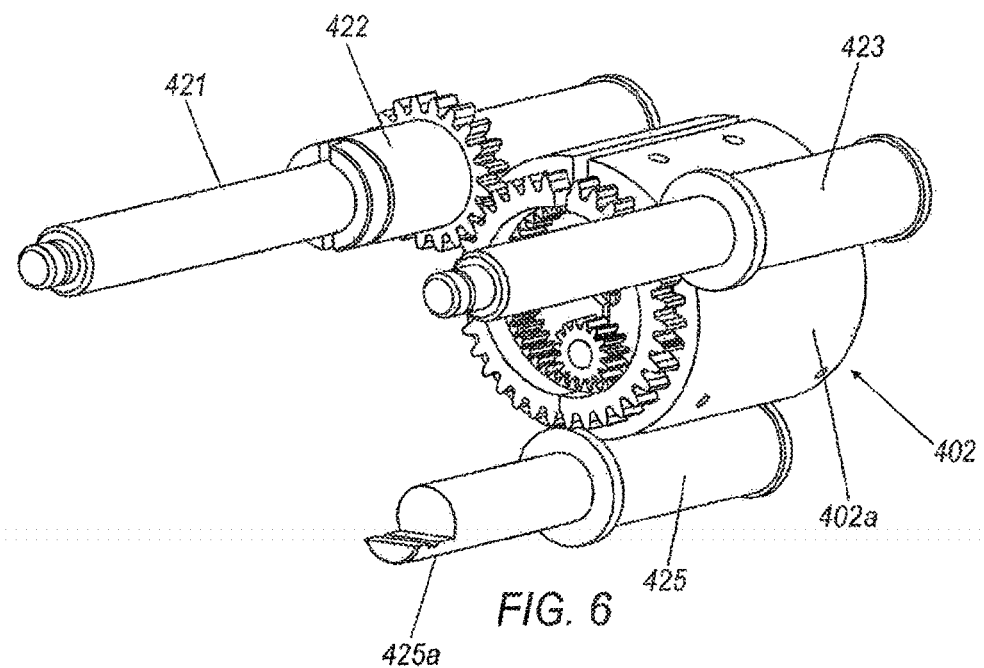
FIG. 6 is a rear perspective view of the exemplary drive apparatus of FIG. 4, with a support plate removed.

Turning now to FIGS. 4-11, exemplary drive apparatus 400 is illustrated in further detail. As noted above, the drive apparatus 400 may include a disposable mechanism 402 for contacting and driving an elongate member, e.g., a guidewire or catheter. An associated drive mechanism 404 may generally be configured to be kept separate from the disposable mechanism 402, at least to an extent allowing the drive mechanism 404 to be kept out of a sterile environment associated with the elongate member and surgical procedure. As best seen in FIGS. 4-6, the disposable mechanism 402 may be supported between two idle rollers 421, 423, and a driving roller 425 which is configured to rotate the disposable mechanism 402 to impart rotational motion to the elongate member, as will be described further below. Moreover, the idle roller 421 may include a driving gear 422 for selectively imparting axial motion, i.e., insertion or retraction, of an elongate member, as will also be further described below.

Figure 9:
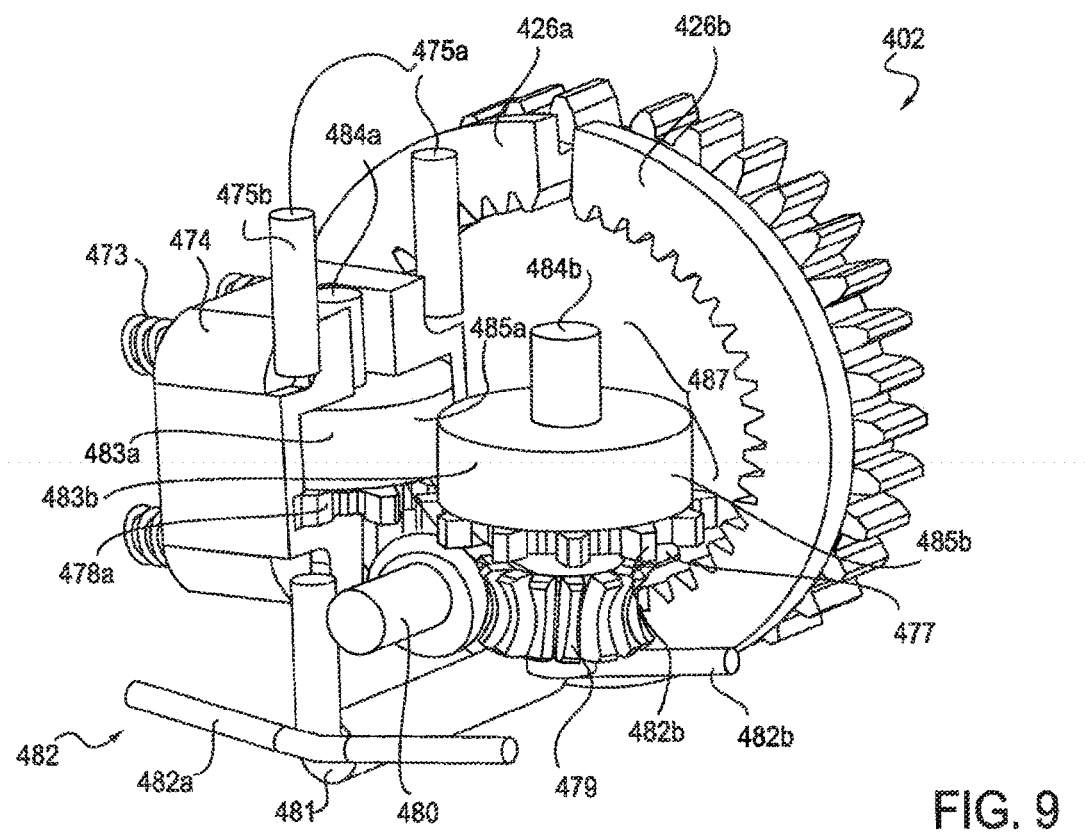
FIG. 9 is a front perspective view of the disposable device of FIG. 7, with the disposable device in an open position and shown without a split housing.

The disposable portion 402 may include a roller assembly 487, e.g., comprising one or more rollers 483 that are configured to impart axial motion to the elongate member along a first continuous surface 485a. For example, as best seen in FIG. 9, a roller 483a and a second roller 483b each define generally cylindrical surfaces 485a, 485b that are configured to maintain contact with the elongate member during axial motion, i.e., caused by rotation of the rollers 483. The drive apparatus 400 may further include a roller support 421, 423, 425 configured to rotate the roller assembly 487, i.e., at least one of the rollers 483, thereby imparting rotational motion to the elongate member. For example, as will be described further below, the rollers 483 may generally be supported within the clamps 401, 403 of the disposable portion, e.g., via a saddle 474 or by the clamps 401, 403 themselves, such that the rollers 483 may be rotated about an axis defined by the elongate member. Moreover, the roller support 421, 423, 425 may be configured to rotate the roller assembly 487 about a second continuous surface 485b configured to maintain contact with the roller support 421, 423, 425 during rotational motion, thereby permitting generally any magnitude of rotational motion. Moreover, the roller assembly 487 and roller support 421, 423, 425 may be configured to impart axial and rotational motion independently of one another, such that a first one of the roller assembly 487 and the roller support 421, 423, 425 imparts their associated motion regardless of a presence or absence of motion by the other of the roller assembly and the roller support 421, 423, 425. More specifically, as will be described further below the rollers 483 may generally rotate about their respective spindles to provide axial motion, regardless of whether the spindles themselves are being rotated about the axis of the elongate member.

Figure 7:
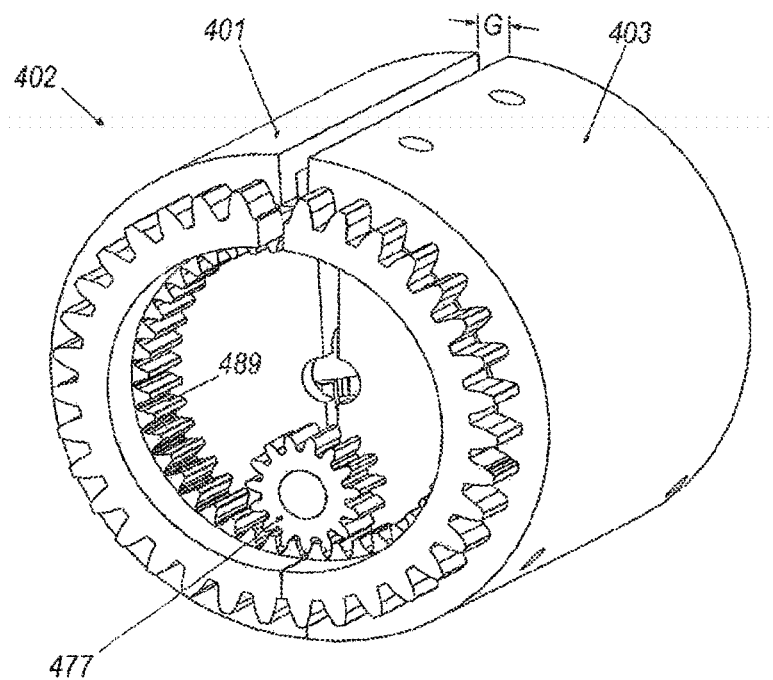
FIG. 7 is a rear perspective view of a disposable device for the exemplary drive apparatus of FIG. 4, with the disposable device in an open position.

Turning now to FIG. 7, the disposable drive mechanism 402 may include a left clamp 401 and a right clamp 403, as best seen in FIG. 7. The left and right clamps 401, 403 may be connected to each other with a compliant member 482 configured to maintain the left and right clamps 401, 403 together in an open position as illustrated in FIG. 7. More specifically, in the open position the left and right clamps 401, 403 are held together along a lower portion and are spaced apart by a gap G along an upper portion of the clamps 401, 403. In one exemplary illustration, the compliant member 482 includes first and second memory wires 482a, 482b, e.g., nitinol wires, which generally act similar to a spring in holding the clamps together in the open configuration shown in FIG. 7. The memory wires 482a, 482b may generally provide a locating feature for the roller assembly 487, thereby generally positioning the rollers 483a, 483b within the clamps 401, 403, as best seen in FIG. 9.

Referring now to FIG. 9, the disposable mechanism 402 is illustrated with the left and right clamps 401, 403 (not shown in FIG. 9) removed. The disposable drive mechanism 402 includes a roller assembly 487, e.g., having one or more rollers 483a, 483b for imparting axial motion to the elongate member. As shown in FIG. 9, two rollers 483a, 483b may be configured to receive an elongate member (not shown in FIG. 9) therebetween. More specifically, the rollers 483 may each rotate about corresponding spindles 484a, 484b. Moreover, as will be described further below the rollers 483a, 483b may each have a plurality of geared teeth 478a, 478b which are meshingly engaged such that the rotation of the rollers 483a, 483b is generally coordinated. The rollers 483a, 483b may each be generally round, thereby defining respective continuous surfaces 485a, 485b about the generally cylindrical rollers 483 for engaging the elongate member. More specifically, an axial movement of any distance may be applied by the rollers 483a, 483b, since the rollers 483a, 483b may continuously turn about the spindles 484 without limitation. Accordingly, axial motion of the elongate member is not limited by any range of motion of any component of the drive apparatus 400, allowing the drive apparatus 400 to provide an axial movement in either direction of any magnitude while maintaining constant contact with the elongate member, i.e., by way of the generally looped or continuous surfaces 485a, 485b of the rollers 483a, 483b.

The roller assembly 487 may be supported in a roller support 421, 423, 425 configured to rotate the rollers about an axis perpendicular to the spindles 484 of the rollers 483. For example, the spindle 484a of the roller 483a may be supported in a saddle 474 that is engaged with an interior surface of one of the clamps 401, 403 (not shown in FIG. 9) by way of a plurality of springs 473. Radially inward movement of the saddle 474 away from the interior surface may be limited by stop pins 475, which may engage an interior side of the saddle 474 to generally limit radially inward movement of the saddle 474 and the roller 483a, thereby limiting force applied by the roller 483a to the elongate member when the elongate member is positioned between the rollers 483a, 483b. The spindle 484b of the other roller 483b may be supported in the corresponding one of the clamps 401, 403 (not shown in FIG. 9). Accordingly, the spindle 484b may be generally fixed within the clamps 401, 403 while the spindle 484a may be movable by way of the springs 473 to provide a clamping force upon the elongate member.

Figure 8:
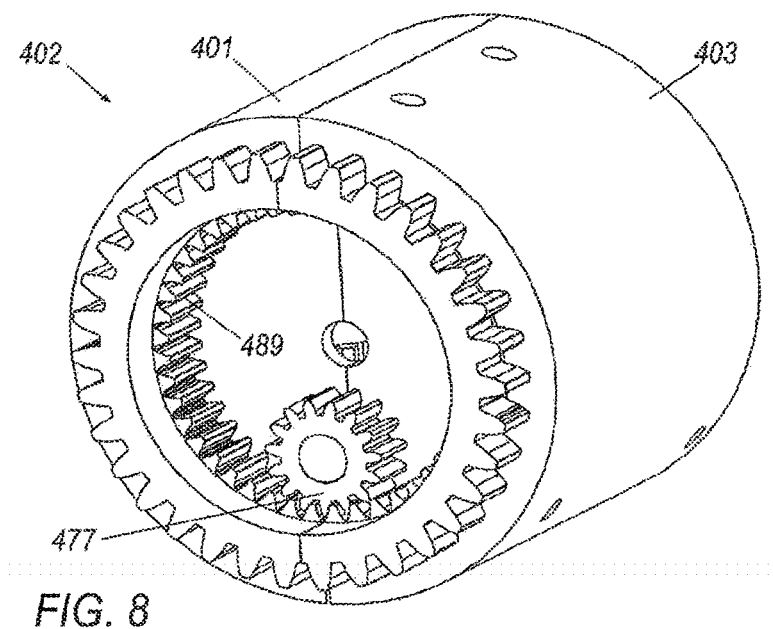
FIG. 8 is a rear perspective view of the split clamp assembly of FIG. 7, with the disposable device in a closed position.

The disposable device 402 may further comprise gear halves 426a, 426b which define an inner toothed surface 489 engaging a drive pinion 477 (see FIGS. 7 and 8). The drive pinion 477 may be engaged with a worm gear 479 by way of worm 480, wherein the worm 480 is fixed for rotation with the drive pinion 477. A location shaft 481 may be provided to assist with locating the above components within the clamps 401, 403, as will be described further below. Additionally, a compliant element 482 may be provided which generally provides a spring force urging the clamps 401, 403 toward an open position, e.g., as seen in FIG. 7.

Figure 10:
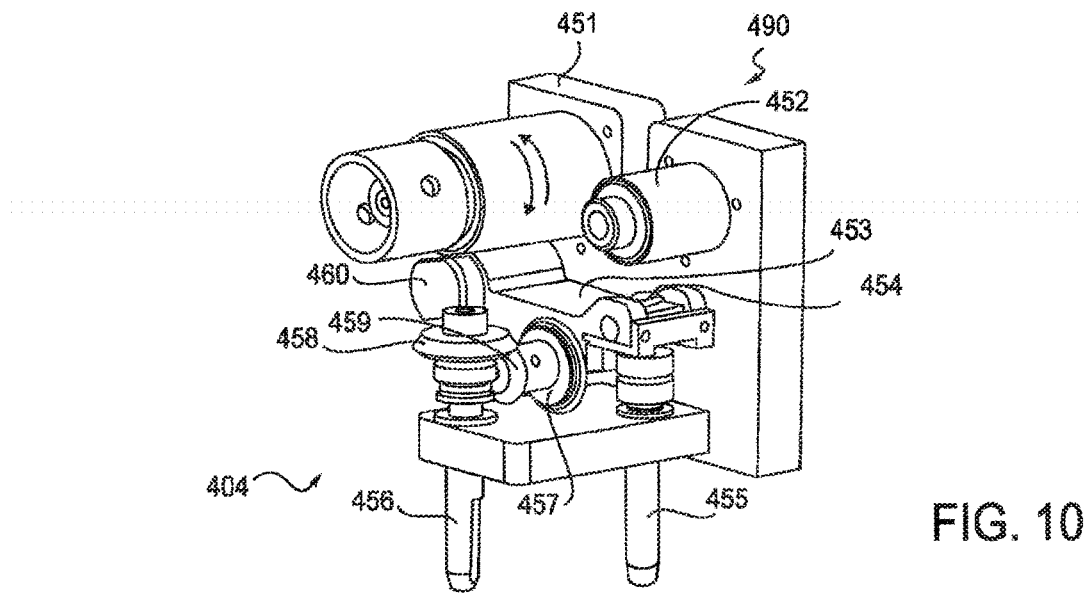
FIG. 10 is a rear perspective view of a drive mechanism for the exemplary drive apparatus of FIG. 4.
Figure 11:
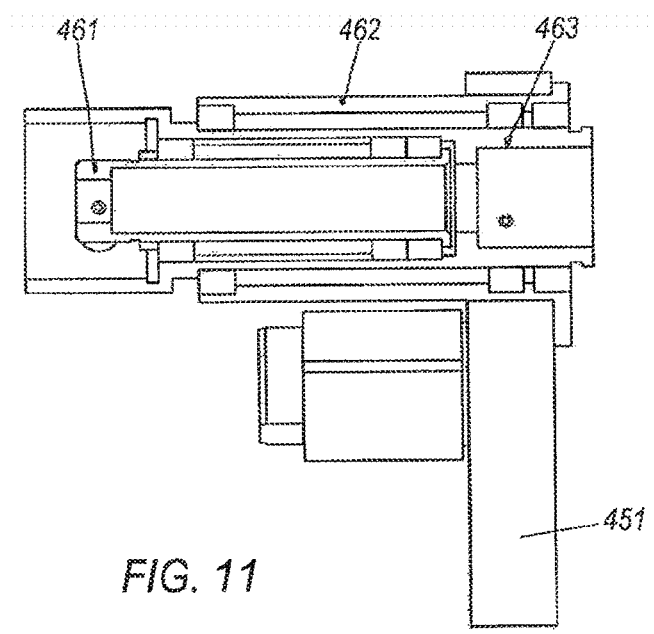
FIG. 11 is a section view of the exemplary drive mechanism taken through line 11-11 in FIG. 10.

The driving mechanism 404, as best seen in FIGS. 10 and 11, may include a front plate 451 having a channel 490 through which an elongate member may be received during operation. The driving mechanism may further include a right idle roll rotational assembly 452 which corresponds to right idle roller 423 (see FIGS. 4-6). Additionally, a lever 453 is located on the front plate 451 by way of a pivot shaft 460, about which the lever 453 may be pivoted by way of a threaded member 454, which may be a driving screw. The driving mechanism 404 may include driving shafts 455 and 456, which may be received within corresponding drive mechanisms (not shown) associated with the instrument driver 108 supporting the instrument 109 (see FIG. 3). A driving roll rotational assembly 457 supports bevel gears 458 and 459, which are engaged to transfer rotational motion of the driving shaft 456 to driving roller 425 (see FIGS. 4 and 5). A left idle roll bushing 461 and driving gear bushing 463 may be supported in a housing 462 mounted to the support plate 451, as will be described further below.

The drive apparatus 400 may generally integrate a plurality of actuating mechanisms together. The drive apparatus 400 may include a mechanism for opening and closing to facilitate loading and unloading of an elongate member, e.g., a guidewire or a catheter. As will be described further below, the clamps 401, 403 may generally be opened to allow top loading of an elongate member, and may thereby facilitate loading of the elongate member without requiring threading the elongate member axially through the drive apparatus 400. The drive apparatus may also include a mechanism for inserting and retracting the elongate member, i.e., in an axial direction. Moreover, the drive apparatus 400 also includes a mechanism for imparting rotational motion to the elongate member. Additionally, as will be described further below, the drive apparatus 400 may provide axial motion and rotational motion simultaneously, and in an "infinite" manner. More specifically, as will be seen below the insertion and rotational motion is provided by continuous drive surfaces, e.g., the generally round or looped roller surfaces 485a, 485b and the toothed gear engagement between the drive pinion 477 and gear halves 426a, 426b. Accordingly, a generally continuous axial or rotational motion may be provided without releasing the elongate member during the motion. In other words, the rotational and insertion motions are not limited by any range of motion of the drive apparatus 400 or components thereof. Moreover, the rotational and axial motion may be provided independent of the other, i.e., one of or both of the rotational and axial motion may be applied to the elongate member at any given time.

Referring now to FIGS. 6 and 7, the use and operation of the drive apparatus 400 will be described in further detail. Initially the drive apparatus 400 may be in the open position, i.e., where the disposable portion 402 defines a gap G between the clamps 401, 403 as best seen in FIG. 7. While the disposable portion 402 is in the open position, the elongate member, e.g., a guidewire or catheter (not shown in FIG. 6 or 7), may be placed between the rollers 483a, 483b supported from below by the compliant members 482. An end portion 425a of driving roller 425 (see FIG. 6), may be located in the driving roll assembly 457 and can be moved up and down by rotation of the lever 453, which rotates about the pivot shaft 460, as best seen in FIG. 7. The lever 453 may be actuated by threaded member 454. Accordingly, the driving roller 425 may selectively open and close the disposable portion 402. More specifically, when the driving roller 425 is in an upper position as defined by the pivoting of the lever 453, the disposable portion 402 will be closed, as seen in FIG. 8. When the driving roller 425 is moved downward to a lower position, the driving roller 425 generally allows the compliant element 482 to urge the clamps 401, 403 apart at the upper portion, defining the gap G as best seen in FIG. 7. Upon movement of the driving roller 425 upward, the disposable portion 402 is forced to close. For example, an engagement portion 425b of the driving roller 425 may come into contact with one or both clamps 401, 403, thereby forcing the clamps 401, 403 together at the upper portion, closing the gap G as seen in FIG. 8.

Upon closure of the disposable portion 402, the elongate member may be held between the rollers 483a, 483b with a force that is generally limited by springs 473, as best seen in FIG. 9. More specifically, the springs 483 may generally act upon an inner surface of one of the clamps 401, 403 (not shown in FIG. 9), urging the roller 483a which is supported in the saddle 474 toward the other roller 483b. Accordingly, a desired force of the rollers 483a, 483b may be adjusted based upon the spring force imparted by the springs 473.

Turning now to FIGS. 6 and 10, a rotational motion imparted by the drive apparatus 400 to an elongate member will be described in further detail. The roller 425 may be rotated via the shaft 456, e.g., though bevel gears 458 and 459, as best seen in FIG. 10. Rotation of the driving roller 425 in turn rotates the disposable portion 402 via friction between the engagement portion 425b of the roller 425 and an outer surface 402a of the disposable portion 402, as best seen in FIG. 6. Motion may be imparted to the disposable portion via other mechanisms as well. Merely as an example, motion may be transferred from the roller 425 to the disposable portion 402 using corresponding toothed surfaces on the roller 425 and the disposable portion 402, similar to a geared arrangement.

Turning now to FIGS. 9-11, the axial motion of the drive apparatus 400 is described in further detail. FIG. 11 illustrates a cross section of the holders for left idle roller 423 and driving gear 422 (see FIG. 3). More specifically, left idle roll 423 is located by bushing 461 and driving gear 422 is located by bushing 463. The bushing 463 may have a driving mechanism (not shown) for selectively rotating the driving gear 422. Rotation of the driving gear 422 (see FIG. 3), which is engaged with an outer toothed surface of gear halves 426a, 426b, will thereby rotate the gear halves 426a, 426b. The gear halves 426a, 426b when in the closed position (i.e., as in FIG. 8) may form a gear that rotates in response to the driving gear 422 (see FIG. 6). The gear halves 426a, 426b in turn actuates gear 477 as best seen in FIGS. 7 and 8. The gear 477 is located on the worm 480, as illustrated in FIG. 9. Rotation of the worm 480 in turn drives worm gear 479. The worm gear 479 actuates one of the rollers 483b. The other roller 483a rotates in response to the roller 483b, as they are connected with the corresponding gears 478a, 478b. The surfaces 485a, 485b of the rollers 483a, 483b may generally be designed to ensure substantially slipless contact with the elongate member, such that the turning of the rollers 483a, 483b imparts axial motion directly to the elongate member.

To enact simultaneous axial and rotational motion of the elongate member, shaft 456 (see FIG. 10) and drive gear 422 (see FIG. 6) may be driven simultaneously. Moreover, the instrument 109 may include interfaces for the shaft 456 and drive gear 422 that allow for selective rotation of each, facilitating independent axial and rotational motion. Rotational speeds of the components of the drive apparatus 400 can be optimized as needed to suit any given application, e.g., by altering the interfaces between the various rotational parts, e.g., by adjusting the geared arrangements to ensure reasonable rotational speeds of the components based upon typical axial and rotational movement for the given application.

Figure 12A:
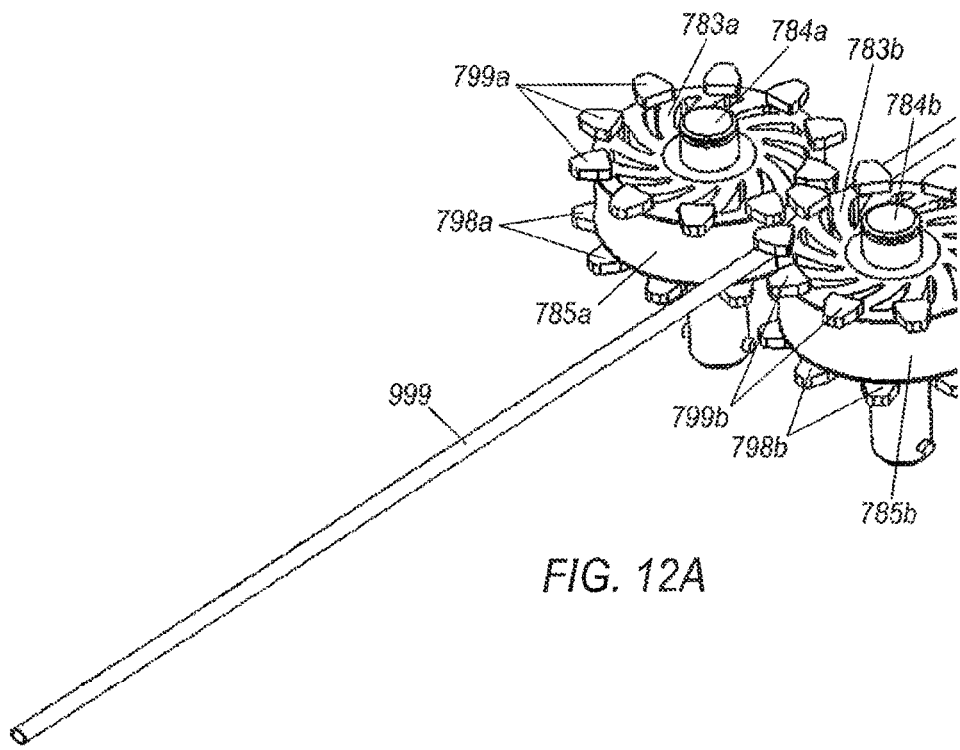
FIG. 12A is a perspective view of another roller assembly with an elongated member, according to an exemplary illustration.
Figure 12B:
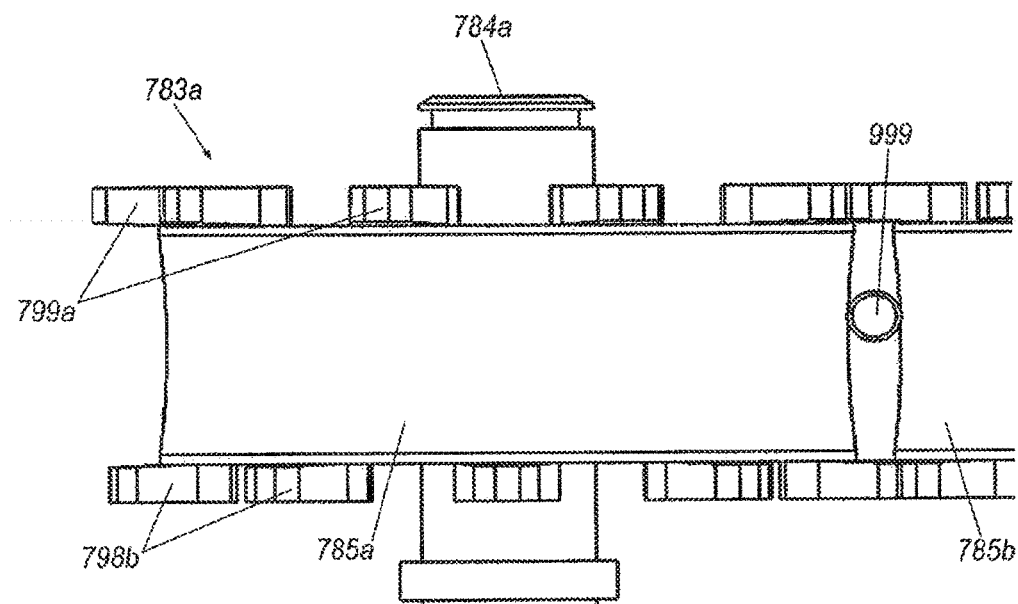
FIG. 12B is a front perspective view of the exemplary roller assembly of FIG. 12A.

Turning now to FIGS. 12A and 12B, another set of exemplary rollers 783a, 783b is illustrated with an elongate member 999, e.g., a guidewire. The rollers 783a, 783b may each define generally cylindrical continuous surfaces 785a, 785b, and may rotate about spindles 784a, 784b, e.g., similar to rollers 483a, 483b. Moreover, the rollers 783a, 783b may each define a plurality of upper teeth 799a, 799b, as well as a plurality of lower teeth 789a, 798b. The upper teeth 799a of the roller 783a may generally mesh with the upper teeth 799b of the roller 783b, and the lower teeth 798a of the roller 783a may generally mesh with the lower teeth 798b of the roller 783b, thereby generally preventing an elongate member received between the rollers 783a, 783b, e.g., guidewire 999, from slipping out between the rollers 783a, 783b. Moreover, the upper and lower teeth 799, 798 may still allow for top loading of an elongate member such as the guidewire 999. For example, at least one of the rollers 783a, 783b may be supported in a saddle, e.g., as described above regarding roller 483a, which allows enough lateral displacement of the roller 783a or 783b to be moved to temporarily open a gap between the upper teeth 799 through which the elongate member can be laid between the rollers 783a, 783b.

Operator workstation 112, electronics rack 114 and/or drive apparatus 400 may include a computer or a computer readable storage medium implementing the operation of drive and implementing the various methods and processes described herein, e.g., process 1300. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

The drive apparatus 400 may advantageously use disposable materials in the construction of the disposable mechanism 402, e.g., an injection molded plastic material. Additionally, the disposable mechanism is relatively short in an axial direction associated with the elongate member, minimizing wasted length, i.e., the portion of the elongate member that must be gripped or held by the drive apparatus 400 during operation. The minimal length of the drive apparatus 400 may generally be due in part to the containment of the driving mechanisms of the disposable portion 402 within the clamps 401, 403. Additionally, the drive apparatus employs separate driving mechanisms, e.g., rollers 483a, 483b and the toothed gear engagement between the drive pinion 477 and gear halves 426a, 426b, that allow for independent control of the axial motion and rotational motion. Moreover, the drive apparatus mechanism 400 provides generally "infinite" motion due to the looped or round surfaces of the rollers 483a, 483b and the toothed gear engagement between the drive pinion 477 and gear halves 426a, 426b, thereby allowing for application of any magnitude of axial or rotational motion without having to release the elongate member. Accordingly, axial and rotational motion of the elongate member are not limited by any range of motion of the drive apparatus 400. Finally, the split clamps 401, 403 of the disposable portion allows for top loading of the elongate member, such that the elongate member need not be threaded through the drive mechanism during installation of the elongate member.

The exemplary illustrations are not limited to the previously described examples. Rather, a plurality of variants and modifications are possible, which also make use of the ideas of the exemplary illustrations and therefore fall within the protective scope. Accordingly, it is to be understood that the above description is intended to be illustrative and not restrictive.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "the," etc. should be read to recite one or more of the indicated elements unless a claim recites an explicit limitation to the contrary.

What is claimed is:

1. A drive apparatus, comprising:
    a housing defining a housing space therein;
    a roller assembly comprising one or more rotatable rollers and configured to receive an elongate member;
    a driving roller having a first portion disposed within the housing space and a second portion extending outside the housing space;
    a first driving shaft configured to rotate the one or more rollers, wherein rotation of the one or more rollers imparts axial motion to the elongate member along an elongate axis of the elongate member; and
    a second driving shaft configured to rotate the driving roller, wherein rotation of the driving roller imparts rotation to the elongate member about the elongate axis.

2. The drive apparatus of claim 1, wherein rotation of the first driving shaft and the second driving shaft is robotically controlled.

3. The drive apparatus of claim 1, wherein the first driving shaft and the second driving shaft are configured for placement within corresponding drive mechanisms of a robotic instrument driver.

4. The drive apparatus of claim 1, wherein the one or more rollers impart the axial motion independently of the rotational motion imparted to the elongate member by the driving roller.

5. The drive apparatus of claim 1, further comprising a disposable barrel positioned outside the housing space.

6. The drive apparatus of claim 1, wherein the one or more rollers are configured to maintain contact with the elongate member during the axial motion.

7. A drive apparatus for an elongated member, the drive apparatus comprising:
    a housing defining a housing space therein;
    a roller assembly configured to impart axial motion to the elongate member; and
    a roller support configured to rotate the roller assembly to impart rotational motion to the elongate member, the roller support configured to be partially disposed within the housing space,
    wherein the axial motion and the rotational motion are imparted independently of one another.

8. The drive apparatus of claim 7, wherein the roller assembly is configured to operate in an open configuration in which the elongate member may be placed within the roller assembly, or in a closed configuration in which the roller assembly is configured to impart rotational motion to the elongate member.

9. The drive apparatus of claim 7, wherein the roller assembly is configured to maintain contact with the elongate member during axial motion.

10. The drive apparatus of claim 7, wherein the roller assembly comprises one or more rollers configured to facilitate the imparting of the axial motion to the elongate member, and wherein the drive apparatus further comprises a pair of clamps at least partially surrounding the one or more rollers.

11. The drive apparatus of claim 10, wherein the pair of clamps are configured to selectively open to define a gap, allowing the elongate member to be top loaded and received through the gap.

12. The drive apparatus of claim 7, wherein the roller support comprises a driving roller configured to rotate the roller assembly.

13. A drive apparatus, comprising:
    a housing defining a housing space therein;
    a pair of clamps adjacent to the housing and configured to receive an elongate member; and
    a plurality of support rollers positioned partially within the housing space and configured to:
    support and rotate the pair of clamps, and
    operate in an open configuration or a closed configuration, wherein, in the closed configuration, the plurality of support rollers are configured to rotate the pair of clamps about an axis of the elongate member.

14. The drive apparatus of claim 13, wherein, in the open configuration, the plurality of support rollers are configured to position the pair of clamps to allow the elongate member to receive the elongate member.

15. The drive apparatus of claim 14, wherein the elongate member is configured to be top loaded between the pair of clamps.

16. The drive apparatus of claim 13, wherein, in the closed configuration, the plurality of support rollers are configured to rotate the elongate member via rotation of the pair of clamps.

17. The drive apparatus of claim 13, wherein the plurality of support rollers are configured to maintain contact with the pair of clamps.

18. The drive apparatus of claim 13, wherein the plurality of support rollers comprise a driving roller and two idle rollers.

19. The drive apparatus of claim 13, wherein the plurality of support rollers comprise a driving roller configured to rotate the pair of clamps.

* * * * *